United States Patent [19]
Colliot

[11] Patent Number: 5,942,533
[45] Date of Patent: Aug. 24, 1999

[54] METHOD FOR CONTROLLING ACRIDIDAE

[75] Inventor: François Colliot, Fontaines Saint Martin, France

[73] Assignee: Rhone-Poulenc Agrochimie, Lyons, France

[21] Appl. No.: 08/913,812

[22] PCT Filed: Mar. 22, 1996

[86] PCT No.: PCT/FR96/00433

§ 371 Date: Jan. 7, 1998

§ 102(e) Date: Jan. 7, 1998

[87] PCT Pub. No.: WO96/29872

PCT Pub. Date: Oct. 3, 1996

[30] Foreign Application Priority Data

Mar. 24, 1995 [FR] France ................................. 95 03741

[51] Int. Cl.$^6$ ............................. A01N 43/40; A01N 43/56
[52] U.S. Cl. ........................................... 514/407; 514/341
[58] Field of Search ................................. 514/341, 407

[56] References Cited

U.S. PATENT DOCUMENTS

| | | | |
|---|---|---|---|
| 5,232,940 | 8/1993 | Hatton et al. ............................ | 514/407 |
| 5,306,694 | 4/1994 | Phillips et al. .......................... | 504/253 |

FOREIGN PATENT DOCUMENTS

| | | |
|---|---|---|
| 2108383 | 4/1994 | Canada . |
| 0214477 | 3/1987 | European Pat. Off. . |
| 0234119 | 9/1987 | European Pat. Off. . |
| 0295117 | 12/1988 | European Pat. Off. . |
| 0500209 | 8/1992 | European Pat. Off. . |
| 0679650 | 11/1995 | European Pat. Off. . |
| 94/21606 | 9/1994 | WIPO . |

OTHER PUBLICATIONS

Derwent WPI, week 9327, 93–218148 [27], 1993.

*Primary Examiner*—Allen J. Robinson
*Attorney, Agent, or Firm*—Burns, Doane, Swecker & Mathis, L.L.P.

[57] ABSTRACT

A method for controlling acridians comprising treating strips of land separated by untreated strips of land with an active ingredient having the formula:

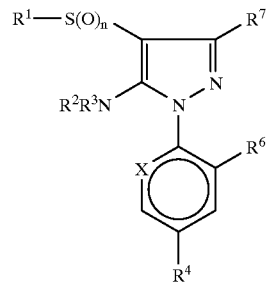

(I)

wherein n is 0, 1 or 2; X is N or $CR^5$; $R^1$ is $C_1$-$C_4$ alkyl or $C_1$-$C_4$ haloalkyl; $R^2$ and $R^3$, which are identical or different, are H or $C_1$-$C_4$ alkyl, optionally substituted with halogen, hydroxy, alkoxy, imino or alkylimino; $R^4$ is halogen, halomethyl, halomethoxy or $SF_5$; $R^5$ and $R^6$, which are identical or different, are H or halogen, at least one of them being other than H when X is $CR^5$; and $R^7$ is cyano or halogen or, when $R^1$ is $C_1$-$C_4$ haloalkyl, $R^7$ is H, halogen, alkyl, haloalkyl or cyano.

22 Claims, No Drawings

METHOD FOR CONTROLLING ACRIDIDAE

This application is a 371 of PCT/FR96/00433, filed Mar. 22, 1996.

The subject of the present invention is a method for controlling acridians.

The control of acridians using insecticides from the 1-phenylpyrazole family has already been proposed.

In general terms, it is desirable to decrease the doses of active material applied both for environmental reasons and economic reasons, and one aim of the invention is to satisfy this need without harming the effectiveness.

It is also desirable to accelerate the application of antiacridian products on account of the urgency of interventions due to the seriousness of the damage caused by acridians. Another aim of the invention is to satisfy these new needs.

It has now been found that these aims could be achieved by means of the method according to the invention, which consists in applying a composition comprising an active material of formula (I):

$$\text{(I)}$$

$$\begin{array}{c} R^1-S(O)_n \quad\quad R^7 \\ \diagdown \quad\quad \diagup \\ R^2R^3N \quad N \\ \quad\quad | \\ \quad\quad \text{Ar}(X, R^4, R^6) \end{array}$$

in which:
n is equal to 0, 1 or 2; and
X represents a nitrogen atom, or alternatively a $CR^5$ group; and
$R^1$ is a linear or branched $C_1$-$C_4$ alkyl group or a $C_1$-$C_4$ haloalkyl group; and
$R^2$ and $R^3$, which may be identical or different, represent a hydrogen atom or a linear or branched $C_1$-$C_4$ alkyl group which is optionally substituted, in particular with a halogen atom or a hydroxyl, alkoxy, imino or alkylimino group; and
$R^4$ is a halogen atom or a halomethyl, halomethoxy or $SF_5$ group; and
$R^5$ and $R^6$, which may be identical or different, represent a hydrogen or halogen atom, at least one of them being other than a hydrogen atom when X is a $CR^5$; and
$R^7$ represents a cyano group or a halogen atom or, when $R^1$ represents a $C_1$-$C_4$ haloalkyl group, $R^7$ represents a hydrogen or halogen atom or an alkyl, haloalkyl or cyano group;
the said application being carried out on strips of land which are spaced apart from each other.

According to a particularly advantageous variant of the invention, the compound of formula (I) used in the invention is 5-amino-3-cyano-1-[2,6-dichloro-4-(trifluoromethyl) phenyl]-4-[(trifluoromethyl)sulphinyl]-1H-pyrazole, also known as fipronil.

The compounds of formula (I) may be prepared according to one of the methods described in European patent applications EP 234,119, EP 295,117, EP 679,650 and in International patent application WO 94/21606 and may be used in the form of formulations or compositions also described in at least one of these same patent applications. Such compositions comprise the active material combined with one or more vehicles, as well as, optionally, formulation additives or adjuvants such as surfactants, dispersing agents, wetting agents, binders and the like.

The compositions used in the method according to the invention generally comprise from 0.001 to 95% by weight of compound of formula (I), preferably from 0.2 to 15% by weight.

These compositions may be applied in the method according to the invention using spraying equipment which is known per se. The application of the compositions to large areas of land generally involves the use of application equipment mounted on a truck, or alternatively on an aeroplane; the use of spraying cannons is advantageous.

The application according to the invention is advantageously carried out on strips of land which may be more or less parallel, these treated strips being arranged at more or less regular intervals from each other. It is practical for the treated strips of land to be separated by untreated strips. The ratio of the widths of the untreated strips to the widths of the treated strips is between 1 and 20, preferably between 3 and 15.

The width of the treated strips is generally chosen in relation to the characteristics of the application equipment, these widths generally being between 50 and 800 m, preferably between 100 and 400 m. The alternating presence of treated strips and untreated strips is also advantageous; this results in particular in an appreciable gain in terms of speed of intervention.

The term treated strip refers to the portion of land receiving the composition applied at a dose corresponding to a dose of active material of between 60 and 100% of the maximum dose applied, preferably of between 80 and 100%. The average dose applied to the treated strips of land is generally the lethal dose of active material, equal to the dose necessary to eliminate acridians found on a given area of land to be treated, over a period of between 1 and 7 days (preferably of between 1 and 2 days). This average dose applied is generally between 2 and 50 g/ha, preferably between 4 and 20 g/ha, for the strips considered.

The term untreated strip refers to a portion of land on which the composition received after the treatment according to the invention gives rise to an amount of active material of between 0 and 50%, generally of between 0 and 20%, of the maximum dose applied to the treated strips. The presence of active material on the untreated strips results from the phenomenon of drift of the spray liquid ejected by the application equipment, especially from an aeroplane, in particular under the effect of the speed of travel of the application equipment and of possible atmospheric turbulence. The amount of active material present on an untreated strip is, in principle, a non-lethal dose.

The treated land is in general land on which acridians are found or are likely to be found. This comprises land of steppe, savannah, forest or prairie type, or alternatively cultivated land.

The acridians which may be controlled by means of the method according to the invention are, in particular, the African migratory locust (*Locusta migratoria*), the red locust (*Nomadacris septemfasciata*) or alternatively the desert locust (*Schistocerca gregaria*).

An important advantage of the invention is that the effectiveness of the method according to the invention remains general despite the fact that a substantial part, or even the majority, of the acridians directly receives no dose or a low dose and/or a non-lethal dose of product of formula (I).

The examples which follow, given as a guide and with no limitation being implied, illustrate the invention and show how it may be implemented.

EXAMPLE 1

This test is performed on an area of 3000 ha of substantially rectangular shape, occupied by shrubby fallow land and watermelon and sorghum crops, and containing a large amount of desert locusts (*Schistocerca gregaria*).

A composition containing 20 g/l of fipronil dissolved in an organic solvent (ULV (Ultra Low Volume) formulation) is used.

The treatment is carried out by an aeroplane flying at an altitude maintained at between 20 and 50 m, at a speed of 160 km/hour and equipped with a suitable spraying device. The spraying device is adjusted so as to deliver an amount of fipronil per hectare equal to 4 g/ha and so as to apply the composition over an estimated land strip width of 200 m.

The aeroplane begins its treatment by flying parallel to the long side of the rectangle of land. On arriving at the end of the first treated strip, the aeroplane simultaneously makes a loop and a 2000 m translation parallel to the short side of the rectangle of land to be treated. It then treats a new strip of land also parallel to the long side of the rectangle of land. An untreated strip 2000 m wide thus lies next to the treated strip. The untreated strip has received an amount of product less than a value equal to 20% of that received by the treated strip.

These operations are repeated until the aeroplane has covered all of the area to be treated, taking into account both the treated strips and the untreated strips.

The results are observed 10 days after the treatment, by sampling and counting the dead acridians. The effectiveness of the treatment is calculated using the ratio of dead acridians/living or dead acridians. An overall effectiveness of greater than 90% is obtained.

EXAMPLE 2

Example 1 is repeated on an area of 2000 ha, occupied by a mixed shrubby formation of crops (watermelon, niébé) and pasture, which shelters an active population of African migratory locusts (*Locusta migratoria*).

The translation made by the plane between the treatment of 2 strips of land is 1000 m, which represents the width of the untreated strips.

The overall effectiveness of the treatment observed after 10 days is greater than 95%.

EXAMPLE 3

Example 1 is repeated, adjusting the aeroplane flying conditions and the spraying device so as to deliver a dose of fipronil per hectare equal to 15 g/ha onto the treated strips, over a treated strip width of 400 m. The overall effectiveness of the treatment observed after 5 days is 100%.

EXAMPLE 4

Example 2 is repeated, adjusting the spraying device so as to deliver a dose of fipronil per hectare equal to 10 g/ha onto the treated strips. The overall effectiveness of the treatment observed after 5 days is greater than 95%.

EXAMPLE 5

Example 1 is repeated, adjusting the spraying device so as to deliver a dose of fipronil per hectare equal to 6 g/ha onto the treated strips and making an aeroplane translation of 500 m between the treatment of 2 strips of land. The same result as in Example 4 is obtained.

I claim:

1. A method of controlling acridians comprising treating strips of land with an effective antiacridian amount of the compound 5-amino-3-cyano-1-[2,6-dichloro-4-(trifluoromethyl)phenyl]-4-[(trifluoromethyl)sulphinyl]-1H-pyrazole, the treated strips of land alternating with untreated strips of land, the ratio of the width of the untreated strips to the width of the treated strips being between 1 and 20, the width of the treated strips being between 50 and 800 m, the untreated strips of land receiving an ineffective antiacridian amount of said compound, said method providing effective control of acridians throughout the area composed of said treated and untreated strips of land.

2. A method according to claim 1, wherein the ratio of the width of the untreated strips to the width of the treated strips is between 3 and 15.

3. A method according to claim 1, wherein the width of the treated strips is between 100 and 400 m.

4. A method according to claim 2, wherein the width of the treated strips is between 100 and 400 m.

5. A method according to claim 1, wherein the treated strips comprise land of steppe, savannah, forest or prairie type.

6. A method according to claim 1, wherein the treated strips comprise cultivated land.

7. A method according to claim 1, wherein the acridians comprise *Locusta migratoria*.

8. A method according to claim 1, wherein the acridians comprise *Nomadacris septemfasciata*.

9. A method according to claim 1, wherein the acridians comprise *Schistocerca gregaria*.

10. A method according to claim 1, wherein the compound 5-amino-3-cyano-1-[2,6-dichloro-4-(trifluoromethyl) phenyl]-4-[(trifluoromethyl)sulphinyl]-1H-pyrazole is applied as a composition comprising from 0.001% to 95% by weight of said compound.

11. A method according to claim 10, wherein the composition comprises from 0.2 to 15% by weight of said compound.

12. A method according to claim 1, wherein the average dose of 5-amino-3-cyano-1-[2,6-dichloro-4-(trifluoromethyl)phenyl]-4-[(trifluoromethyl)sulphinyl]-1H-pyrazole applied to the treated strips is between 2 and 50 g/ha.

13. A method according to claim 12, wherein the average dose applied to the treated strips is between 4 and 20 g/ha.

14. A method according to claim 13, wherein the average dose applied to the treated strips is between 4 and 15 g/ha.

15. A method according to claim 13, wherein the width of the treated strips is between 200 and 400 m.

16. A method according to claim 1, wherein the ratio of the width of the untreated strips to the width of the treated strips is between 2.5 and 10.

17. A method according to claim 15, wherein the ratio of the width of the untreated strips to the width of the treated strips is between 2.5 and 10.

18. A method according to claim 1, wherein more than 90% of acridians throughout the area composed of treated and untreated strips of land are killed.

19. A method according to claim 1, wherein the majority of the acridians throughout the area composed of treated and untreated strips of land directly receive an ineffective antiacridian amount of 5-amino-3-cyano-1-[2,6-dichloro-4-(trifluoromethyl)phenyl]-4-[(trifluoromethyl)stilphinyl]-1H-pyrazole.

20. A method according to claim 1, wherein the compound is applied using a spraying cannon mounted on a truck.

21. A method according to claim 1, wherein the compound is applied by airplane.

22. A method according to claim 1, wherein the treated strips are approximately parallel and arranged at approximately regular intervals.

* * * * *

UNITED STATES PATENT AND TRADEMARK OFFICE
CERTIFICATE OF CORRECTION

PATENT NO. : 5,942,533
DATED : August 24, 1999
INVENTOR(S) : Francois Colliot

It is certified that error appears in the above-identified patent and that said Letters Patent is hereby corrected as shown below:

<u>Title page, Item [57],</u>
Line 20, change "identifical" to --identical--.
Line 24, change "identifical" to --identical--.

Signed and Sealed this

Fourteenth Day of August, 2001

*Attest:*

*Attesting Officer*

NICHOLAS P. GODICI
*Acting Director of the United States Patent and Trademark Office*